United States Patent [19]
Philippo et al.

[11] Patent Number: 6,060,508
[45] Date of Patent: May 9, 2000

[54] BENZYLAMINE DERIVATIVES, THEIR PREPARATION AND THEIR APPLICATION IN THERAPEUTICS

[75] Inventors: Christophe Philippo; Marie Claire Orts, both of Rueil Malmaison; Olivier Crespin, Cergy; Philippe R. Bovy, Mareil Marly, all of France

[73] Assignee: Synthelabo, Le Plessis Robinson, France

[21] Appl. No.: 09/254,121

[22] PCT Filed: Aug. 22, 1997

[86] PCT No.: PCT/FR97/01514

§ 371 Date: Feb. 26, 1999

§ 102(e) Date: Feb. 26, 1999

[87] PCT Pub. No.: WO98/08834

PCT Pub. Date: Mar. 5, 1998

[30] Foreign Application Priority Data

Aug. 29, 1996 [FR] France .................... 96 10549

[51] Int. Cl.[7] .................... A61K 31/34; A61K 31/38; C07D 307/78; C07D 333/52
[52] U.S. Cl. .................... 514/469; 514/443; 549/467; 549/49
[58] Field of Search .................... 549/467, 49; 514/443, 514/469

[56] References Cited

U.S. PATENT DOCUMENTS

| | | |
|---|---|---|
| 4,526,896 | 7/1985 | Scherrer et al. |
| 4,668,690 | 5/1987 | Shutske . |
| 5,250,565 | 10/1993 | Brooks et al. .................... 514/443 |
| 5,308,866 | 5/1994 | Lesieur et al. .................... 514/469 |
| 5,514,718 | 5/1996 | Lewis et al. .................... 514/621 |
| 5,668,180 | 9/1997 | Lesieur et al. .................... 514/630 |
| 5,792,763 | 8/1998 | Fritz et al. .................... 514/228.2 |
| 5,807,889 | 9/1998 | Perregaard .................... 514/469 |
| 5,843,972 | 12/1998 | Dow et al. .................... 514/367 |
| 5,863,396 | 1/1999 | Gaeta et al. .................... 514/443 |

FOREIGN PATENT DOCUMENTS

| | | |
|---|---|---|
| 0 339 950 | 11/1989 | European Pat. Off. . |
| 2 183 536 | 12/1973 | France . |
| 2 370 472 | 6/1978 | France . |
| 0530149 | 3/1993 | Japan . |

*Primary Examiner*—Deborah C. Lambkin
*Attorney, Agent, or Firm*—Finnegan, Henderson, Farabow, Garrett & Dunner, L.L.P.

[57] ABSTRACT

Compounds of general formula (I)

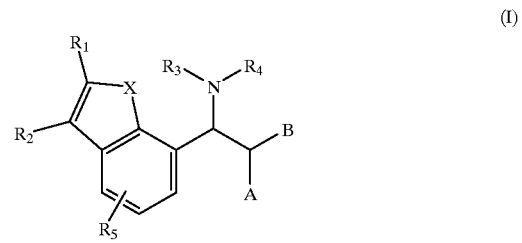

in which:

A represents either a hydrogen atom, a hydroxyl, a $C_{1-6}$ hydroxyalkyl group, a thiol, a $C_{1-6}$ alkylsulphanyl group, an amino group, a $C_{1-6}$ alkylamino group, a di($C_{1-6}$ alkyl)amino group, a $C_{1-6}$ alkylhydroxylamine group, a $C_{1-6}$ alkoxy group, a hydroxylamine group, an N,O-di($C_{1-6}$ alkyl)hydroxylamine group, an azido or a halogen such as fluorine, chlorine or bromine, B represents a hydrogen atom, a linear or branched $C_{1-6}$ alkyl group, a $C_{2-6}$ alkenyl group, a $C_{1-6}$ fluoroalkyl group, a $C_{1-2}$ perfluoroalkyl group, a $C_{1-6}$ alkoxy group, a phenyl group or an oxo group, X represents an oxygen or sulphur atom.

Application in therapeutics.

23 Claims, No Drawings

BENZYLAMINE DERIVATIVES, THEIR PREPARATION AND THEIR APPLICATION IN THERAPEUTICS

This application is a 371 of PCT/FR97/01514 Aug. 22, 1997.

The present invention relates to benzylamine derivatives, their preparation and their application in therapeutics.

The compounds of the present invention correspond to the general formula (I)

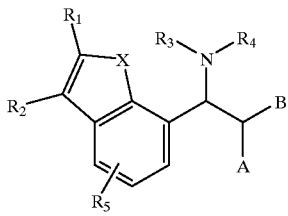

in which:

A represents either a hydrogen atom, a hydroxyl, a $C_{1-6}$ hydroxyalkyl group, a thiol, a $C_{1-6}$ alkylsulphanyl group, an amino group, a $C_{1-6}$ alkylamino group, a di($C_{1-6}$ alkyl)amino group, a $C_{1-6}$ alkylhydroxylamine group, a $C_{1-6}$ alkoxy group, a hydroxylamine group, an N,O-di($C_{1-6}$ alkyl)hydroxylamine group, an azido or a halogen such as fluorine, chlorine or bromine, B represents a hydrogen atom, a linear or branched $C_{1-6}$ alkyl group, a $C_{2-6}$ alkenyl group, a $C_{1-6}$ fluoroalkyl group, a $C_{1-2}$ perfluoroalkyl group, a $C_{1-6}$ alkoxy group, a phenyl group or an oxo group, X represents an oxygen or sulphur atom, $R_1$ and $R_2$, which can be the same or different, represent a hydrogen atom, a halogen such as fluorine, chlorine or bromine, a cyano, a carboxamide, a linear or branched $C_{1-6}$ alkyl group, a $C_{2-6}$ alkenyl group, a $C_{3-6}$ cycloalkyl group, a $C_{1-6}$ alkoxycarbonyl group, a $C_{1-6}$ hydroxyalkyl group, a $C_{1-6}$ alkoxy group, a $C_{1-6}$ alkoxyalkyl group, a $C_{1-6}$ fluoroalkyl group or a $C_{1-2}$ perfluoroalkyl group or $R_1$ and $R_2$, together with the double bond to which they are attached, form a $C_3$–$C_6$ cycloalkenyl ring, a $C_4$–$C_6$ cycloalk-diene-yl ring or a $C_{5-6}$ aryl ring, $R_3$ and $R_4$, which may be the same or different, represent a hydrogen atom, a $C_{1-6}$ alkyl group, a $C_{2-6}$ alkenyl group, a $C_{3-6}$ cycloalkyl group, a $C_{3-6}$ cycloalkenyl group, a $C_{1-6}$ fluoroalkyl group or a $C_{1-2}$ perfluoroalkyl group or $R_3$ and $R_4$ together form a $C_{2-6}$ alkylene group or a $C_{2-6}$ alkenylene group, such as, for example, a —$C_2H_5$ group, a —$C_3H_3$— group or a —$C_4H_8$— group, or $R_3$ and $R_4$, together with the nitrogen atom to which they are attached, form a saturated or unsaturated heterocyclic ring having 2 nitrogen atoms and from 3 to 6 carbon atoms, the available nitrogen atom optionally being substituted by a $C_{1-4}$ alkyl group, such as, for example, a piperazyl ring or imidazolyl ring, or $R_3$ and $R_4$, together with the nitrogen atom to which they are attached, form a saturated or unsaturated heterocyclic ring having an O atom, a N atom and from 3 to 6 carbon atoms, such as, for example, a morpholinyl ring, and $R_5$ represents a hydrogen atom or a halogen, such as fluorine, chlorine or bromine.

The compounds of general formula (I) can contain one or more asymmetric carbon atom. They can thus exist in the form of enantiomers or of diastereoisomers. These isomers and their mixtures, including racemic mixtures, form part of the invention. Suitable pharmaceutically acceptable acids include hydrochloric and fumaric acids.

The compounds of general formula (I) can exist in the form of a free base or of addition salts with pharmaceutically acceptable acids, which also form part of the invention.

The compounds of the invention can be prepared by processes illustrated in the following schemes.

The compounds of formula (I), in particular those in which A represents a hydroxyl group, can be prepared according to the process described in Scheme 1, set out below.

According to this process, an ethenyl derivative of formula IV can be reacted with an oxidizing agent, such as sodium periodate, osmium tetroxide or meta-chloroperbenzoic acid, in basic or acidic medium, so as to form a diol of formula III. The hydroxyl group geminal to the group B can be selectively protected by a protecting group P, in a way known to a person skilled in the art, for example by formation of a silyl ether, so as to obtain a compound of formula II. The hydroxyl group carried by the carbon alpha to the heterocycle of the compound thus obtained can then optionally be activated, in a way known to a person skilled in the art, so as to obtain a nucleofuge group, such as a mesyl or tosyl group or a bromine atom. The compound of formula (I) according to the invention can then be prepared from this compound by reacting the compound with an amine $NMR_3R_4$, followed by deprotection by methods known to a person skilled in the art. The meanings of X, $R_1$, $R_2$, $R_3$, $R_4$, $R_5$ and B in each of the compounds of formulae II and III and in the amine $NHR_3R_4$ are those indicated for the formula (I).

Scheme 1

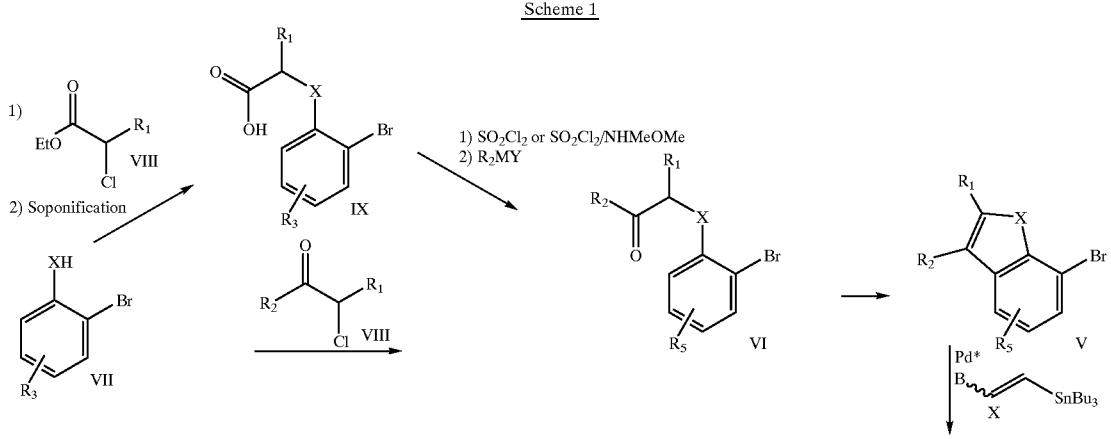

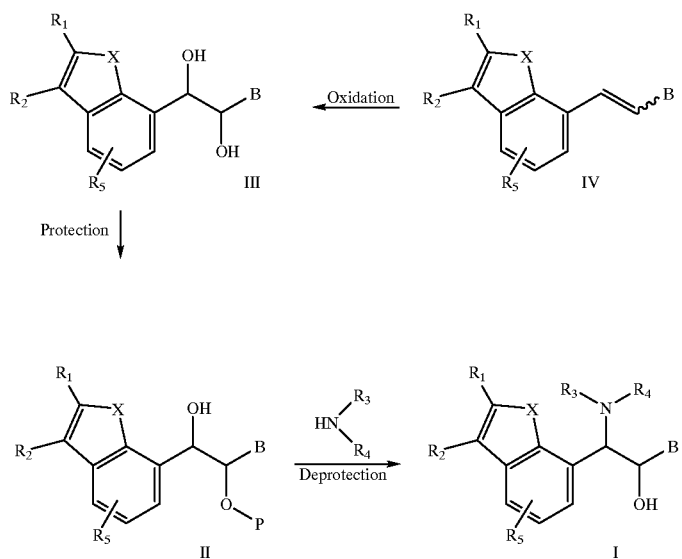

An ethenyl derivative of formula IV can itself be prepared from a brominated derivative of formula V as defined above, by Stille palladium coupling with a compound of formula X, under the conditions defined by McKean, D. R., Parinello, G., Renaldo, A. F. and Stille, J. K., J. Org. Chem., 52, 1987, 492.

Alternatively, an ethenyl derivative of formula IV can be prepared from an aldehyde derivative of formula XI by a Wittig reaction under conditions conventional for a person skilled in the art. The compounds of formula XI can themselves be prepared by formylation of a brominated derivative of formula V in the presence of N,N-dimethylformamide and of butyllithium. The formulation reaction can be carried out in an organic solvent, such as tetrahydrofuran, N,N-dimethylformamide or a mixture of these solvents, according to the following reaction scheme (2):

Scheme 2

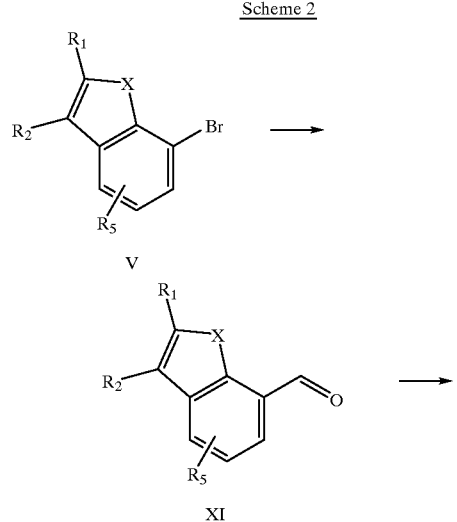

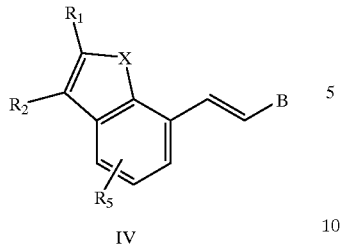

IV

The compounds of formula V can themselves be prepared from α-phenoxyketones or α-thiophenoxyketones of formula VI, which may be reacted with an acid, preferably an inorganic acid, such as polyphosphoric acid or sulphuric acid (Scheme 1). The meanings of X, $R_1$, $R_2$ and $R_5$ in the compounds of formulae V and VI are those indicated for the formula (I).

The compounds of formula VI can be obtained directly from the corresponding phenols or thiophenols of formula VII, which can be reacted with an α-haloketone of formula VIII, preferentially an α-chloroketone. This reaction can be carried out in an organic solvent, such as N,N-dimethylformide, in the presence of potassium carbonate and of an iodide, such as potassium iodide (Scheme 1). The meanings of X, $R_1$, $R_2$ and $R_5$ in the compounds of formulae VI and VII are those indicated for the formula (I).

The compounds of formula VI can also be prepared in two stages, by reaction of a compound of formula VII as defined above in Scheme 1 with an α-haloester of formula VIII, where $R_1$ has the meaning indicated for the formula I, in an organic solvent, such as N,N-dimethylformamide, in the presence of potassium carbonate and of an iodide, such as potassium iodide. This reaction can be followed, after saponification, by the conversion of the intermediate IX thus obtained into the said compound of formula VI. This conversion is typically carried out by the action of thionyl chloride, optionally followed by Weinreb's amine ($SO_2Cl_2$/ $NH(CH_3)(OCH_3)$), under the conditions described by Nahm and Weinreb, Tet. Lett., 22, 3815, 1981, followed by reaction with an organometallic compound of formula $R_2MY$ in which $R_2$ has the meaning indicated for the formula I, M represents a metal and Y represents a halogen, such as chlorine or bromine. This organometallic compound is preferably an organomagnesium compound.

In addition to the process described above, the compounds of formula V in which X represents an oxygen, in particular those in which $R_1$ is a methyl group and $R_2$ is a hydrogen atom, can be prepared according to the following reaction scheme (3)

Scheme 3

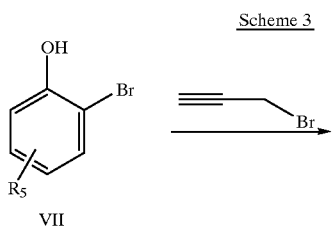

VII

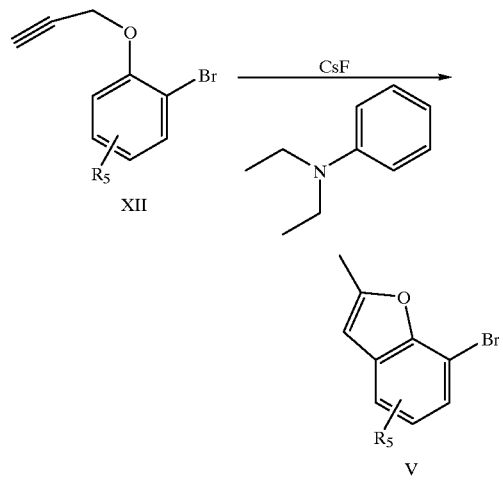

V

According to this process, a compound of formula VII as defined above can be reacted with propargyl bromide. This reaction can be carried out in an organic solvent, such as N,N-dimethylformamide, in the presence of potassium carbonate and of an iodide, such as potassium iodide. The phenoxypropargyl derivative of formula XII thus obtained can then be reacted with diethylaniline in the presence of caesium fluoride, under the conditions described by Ishi, H. et al., Chem. Pharm. Bull., 40, 1992, 1148.

Moreover, the compounds of formula XI, in particular those in which $R_1$ and $R_2$ each represent a hydrogen atom, can be prepared according to the following reaction scheme (4):

Scheme 4

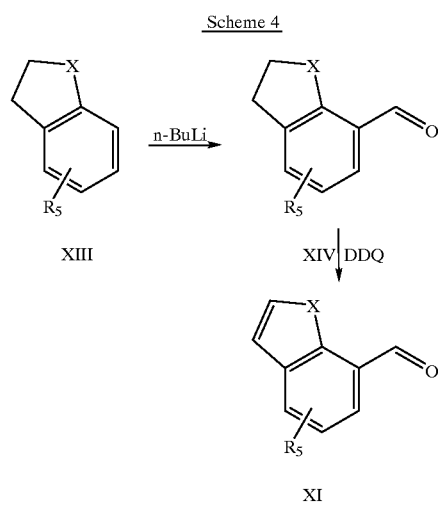

According to this process, a 2,3-dihydrobenzofuran or 2,3-dihydrobenzothiophene of formula XIII can be formulated in the presence of n-butyllithium and N,N-dimethylformamide (DMF), in the optional presence of an organic solvent such as tetramethylenediamine (TMEDA). An aldehyde derivative of formula XIV can then be obtained and treated with 2,3-dichloro-5,6-dicyanocyclohexa-2,5-diene-1,4-dione (DDQ). The compound of formula XI obtained can then be recovered and can be used to prepare the compound of formula (I) according to the process described above.

The compounds of formula (I) according to the invention, in which compounds A is a hydroxyl group, can also be prepared according to the following reaction scheme (5):

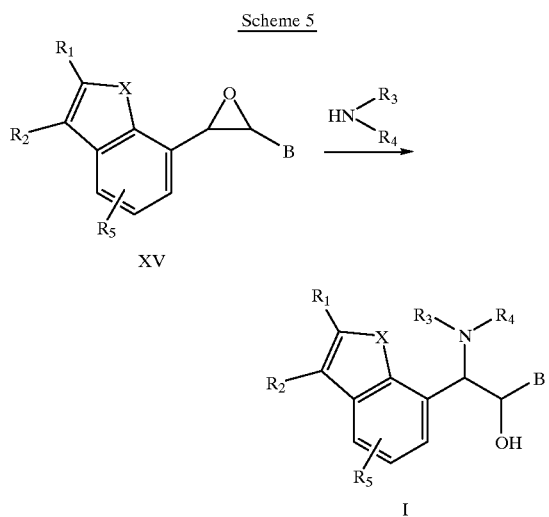

Scheme 5

According to this process, a compound of formula (I) can be prepared by reacting an oxirane derivative of formula XV with an amine $NHR_3R_4$. The meanings of X, $R_1$, $R_2$, $R_3$, $R_4$, $R_5$ and B in the oxirane derivative of formula XV and in the said amine are those indicated for the formula (I).

The oxirane derivative of formula XV can be prepared either by reaction of trimethylsulphonium iodide with the aldehyde of formula XI described above or by the action of a peracid, such as metachloroperbenzoic acid, on the ethenyl derivative of formula IV under conditions conventional for a person skilled in the art.

It is also possible to obtain the oxirane from a ketone of formula XVI.

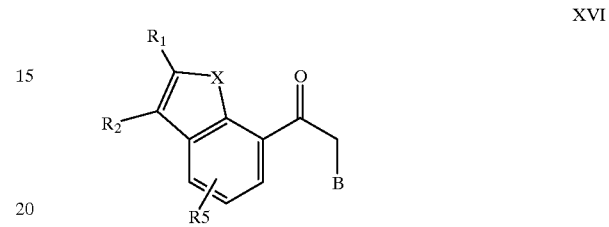

In this case, the ketone can be halogenated at the α position and reduced to the halohydrin which, when treated with a base, can be converted to the oxirane XV.

The compounds of formula (I) in which A is a $C_{1-6}$ alkoxy group and B an oxo group according to the invention can alternatively be prepared according to the following reaction scheme (6):

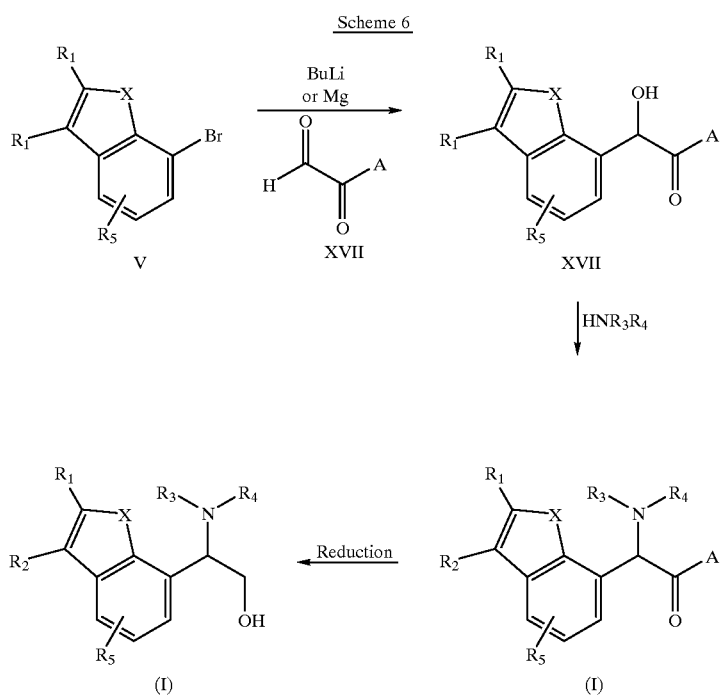

Scheme 6

According to this process, a brominated derivative of formula V as defined above can be metallated, for example by means of butyllithium or, preferably, by the action of magnesium, with the formation of the corresponding Grignard reagent, and then this product may be reacted with an alkyl glyoxylate of formula XVII. The reaction can be carried out in an organic solvent, such as tetrahydrofuran. The hydroxyl group of the compound of formula XVIII can be activated by methods known to a person skilled in the art, so as to obtain a nucleofuge group, such as a mesyl or tosyl group or a bromine atom, and it can then be reacted with an amine $NHR_3R_4$ as defined above.

The compounds of formula (I) in which A is a $C_{1-6}$ alkoxy group and B an oxo group according to the invention can alternatively be prepared by reaction of an organozinc compound or of an organomagnesium compound of the brominated derivative of formula V with a compound obtained by reaction of a secondary amine of formula $HNR_3R_4$, in which the meanings $R_3$ and $R_4$ are those indicated for the formula (I) except for the hydrogen atom, benzotriazole and the alkyl glyoxylate of formula XVII or the monoacetal of glyoxal, according to the process described by Katrizky et al. (Synthesis, 1989, 323; Synthesis, 1990, 1173).

The compounds of formula (I) in which A is a $C_{1-6}$ alkoxy group and B an oxo group can be reduced by conventional methods known to a person skilled in the art to give the compounds of formula (I) in which A is a hydroxyl group and B a hydrogen.

The compounds of formula (I) according to the invention in which A is not a hydroxyl group can also be prepared from the compound of formula I where A is a hydroxyl group by activation of this group, in a way known to a person skilled in the art, so as to obtain a nucleofuge group W, such as a mesyl or tosyl group or a bromine atom, and, by reacting this compound with a nucleophile, according to the following reaction scheme (7):

Scheme 7

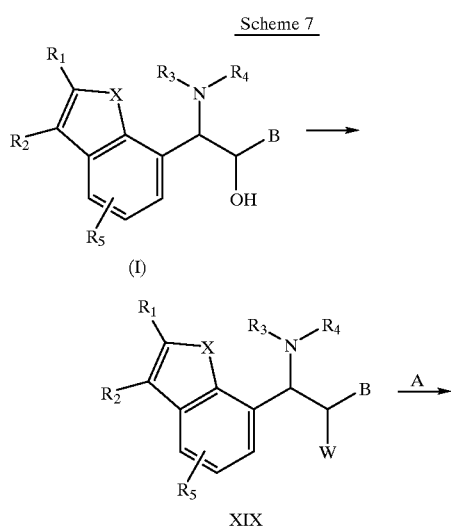

XIX

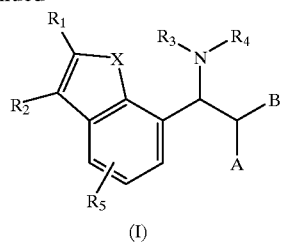

(I)

The nucleophile is typically a source of hydride ions such as $LiAlH_4$ or $NaBR_4$ or a group A as defined above.

The compounds of formula (I) according to the invention in which A is a hydrogen atom can alternatively also be prepared by dehydroxylation of a corresponding compound of formula (I) where A is a hydroxyl group. For example, the dehydroxylation reaction can be carried out, in a way known to a person skilled in the art, by reaction with triethylsilane and trifluoroacetic acid.

The compounds of formula (I) according to the invention, in which A is a hydrogen atom, can also be prepared according to the following reaction scheme (8):

Scheme 8

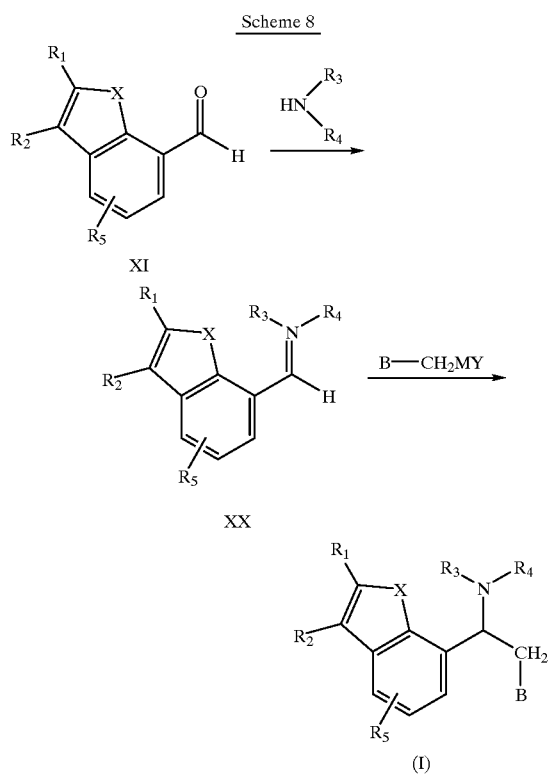

According to this process, the compound of formula (I) can be prepared by reacting a nucleophilic derivative of formula $B-CH_2MY$, in which M represents a metal, Y represents a halogen and B has the meaning indicated for the formula (I), such as, for example, an organomagnesium compound or an organolithium compound, with an imine derivative of formula XX obtained by reaction of a secondary amine of formula $NHR_3R_4$, in which the meanings of $R_3$ and $R_4$ are those indicated for the formula (I) except for the hydrogen atom, with an aldehyde of formula XI. The meanings of X, $R_1$, $R_2$, $R_5$ and B are those indicated for the formula (I).

The starting materials for the syntheses of the compounds of formula (I) are directly available commercially, are known in the literature or can be synthesized by conventional methods known to a person skilled in the art.

The following Examples illustrate the invention. The microanalyses and the NMR and IR spectra confirm the structures of the compounds.

EXAMPLE 1

2,3-Dimethyl-7-(1-diethylamino-2-hydroxyethyl) benzofuran hydrochloride (1) 3-(2-Bromophenoxy)-2-butanone 60 g (347 mmol) of 2-bromophenol, 57.43 g (416 mmol) of potassium carbonate, 57 g (347 mmol) of potassium iodide, 600 ml of N,N-dimethylformamide and 4.34 g (416 mmol) of 3-chloro-2-butanone are introduced into a 1 liter three-necked flask equipped with a reflux condenser. The mixture is heated at 80° C. for 16 hours. 1500 ml of water are added and extraction is then carried out with ethyl acetate (3×400 ml). The organic phases are combined, washed with a molar sodium hydroxide solution (2×500 ml), dried over magnesium sulphate and concentrated. The residue is purified by chromatography on a silica column (elution solvent cyclohexane:ethyl acetate 9:1). 75.07 g (Yield: 89%) of 3-(2-bromophenoxy)-2-butanone (yellow oil) are obtained.

(2) 2,3-Dimethyl-7-bromobenzofuran 25 ml of concentrated sulphuric acid are introduced into a 100 ml three-necked flask, equipped with a thermometer and a 10 ml dropping funnel, and cooled to between −15 and 0° C. by a bath of dry ice in acetone. 3-(2-Bromophenoxy)-2-butanone (5 g, 20.6 mmol) is added dropwise and stirring is continued for 5 min.

The mixture is poured onto crushed ice and extraction is then carried out with ethyl acetate (3×80 ml). The organic phases are combined, dried over magnesium sulphate and concentrated. The residue is purified by chromatography on a silica column (elution solvent: cyclohexane). 4.24 g (Yield: 91%) of 2,3-dimethyl-7-bromobenzofuran are obtained. M.p.=33° C.

(3) 2,3-Dimethyl-7-ethenylbenzofuran 32 g (142 mmol) of 2,3-dimethyl-7-bromobenzofuran, 3.3 g (2.84 mmol) of tetrakis(triphenylphosphine)palladium, 300 ml of toluene and 50 g (156.2 mmol) of tributylvinylstannane are introduced into a 1 liter three-necked flask equipped with a reflux condenser. The mixture is heated at reflux for 3 hours, 1 g of tetrakis(triphenylphosphine) palladium is added and heating is continued for 2 hours. The reaction mixture is allowed to return to room temperature and then 500 ml of ethyl acetate and 500 ml of aqueous sodium hydroxide solution are added. The organic phase is washed with brine, dried over magnesium sulphate and concentrated. The residue is distilled under a vacuum of 0.03 mm of Hg (4 Pa). The fraction distilling between 60 and 78° C. is collected and then purified by chromatography on a silica column (elution solvent: 1% ethyl acetate in cyclohexane). 23.5 g (Yield: 96%) of 2,3-dimethyl-7-ethenylbenzofuran are obtained in the form of a colourless oil.

(4) 2,3-Dimethyl-7-(1,2-dihydroxyethyl)benzofuran 3.86 g (28.6 mmol) of N-methylmorpholine N-oxide, 10 ml of water and 20 ml of acetone are placed in a 100 ml three-necked flask. 2.1 ml of a 1% by mass solution of osmium tetroxide in tort-butanol are added dropwise, followed by a solution of 5.2 g (26 mol) of 2,3-dimethyl-7-ethenylbenzofuran in 10 ml of acetone. The reaction mixture is stirred for 5 hours at room temperature. 100 ml of water are added and extraction is carried out with ethyl acetate (3×150 ml). The organic phases are combined, washed with 100 ml of a 1% sodium bisulphite solution and 100 ml of a 1% sodium bicarbonate solution, dried over magnesium sulphate and concentrated. The residue is purified by chromatography on a silica column (elution solvent: 35% ethyl acetate in cyclohexane). 4.2 g (Yield: 85%) of 2,3-dimethyl-7-(1,2-dihydroxyethyl)benzofuran are obtained in the form of a white solid. M.p.=93–95° C.

(5) 2,3-Dimethyl-7-(2-[tert-butyldimethylsilyloxy]-1-hydroxyethyl)benzofuran 3.7 g (19.3 mmol) of 2,3-dimethyl-7-(1,2-dihydroxyethyl)benzofuran, 200 ml of N,N-dimethylformamide and 2.36 g (34.8 mmol) of imidazole are placed in a 500 ml round-bottomed flask. The mixture is cooled to 0° C., 2.63 g (17.4 mmol) of tert-butylchlorodimethylsilane are added and the mixture is stirred for 2 hours at 0° C. 800 ml of water are added and extraction is carried out with ethyl acetate (3×400 ml). The organic phases are combined, dried over magnesium sulphate and concentrated: The residue is purified by chromatography on a silica column (elution solution: 10% ethyl acetate in hexane). 4.9 g (Yield: 83%) of 2,3-dimethyl-7-(2-[tert-butyldimethylsilyloxy]-1-hydroxyethyl)benzofuran are obtained in the form of an oil.

(6) 2,3-Dimethyl-7-(1-diethylamino-2-[tert-butyldimethylsilyloxy]ethyl)benzofuran 3 g (9.82 mmol) of 2,3-dimethyl-7-(2-[tert-butyldimethylsilyloxy]-1-hydroxyethyl)benzofuran, 50 ml of ethyl ether and 2.2 ml (15.7 mmol) of triethylamine are introduced into a 100 ml round-bottomed flask. The mixture is cooled to −30° C. by a bath of dry ice in acetone and 1.24 ml (15.7 mmol) of mesyl chloride are added. The cooling bath is removed and the reaction mixture is allowed to return to room temperature over 30 minutes. 200 ml of water are added and extraction is carried out with ethyl ether (3×150 ml). The organic phases are combined, dried over magnesium sulphate and concentrated. The residue is transferred, without additional purification, to a 100 ml three-necked flask equipped with a reflux condenser. 20 ml (190 mmol) of diethylamine and 3 ml of chloroform are added and the reaction mixture is heated at reflux for 16 hours. The reaction mixture is cooled to room temperature and concentrated under vacuum, 150 ml of water are added and extraction is carried out with ethyl ether (3×200 ml). The organic phases are combined, dried over magnesium sulphate and concentrated under vacuum. The residue is purified by chromatography on a silica column (elution solvent: 10% methanol in dichloromethane). 2.77 g (Yield 78%) of 2,3-dimethyl-7-(1-diethylamino-2-[tert-butyldimethylsilyloxy]ethyl)-benzofuran are obtained in the form of an oil. (0.5 g of unreacted 2,3-dimethyl-7-(2-[tert-butyldimethylsilyloxy]-1-hydroxyethyl)benzofuran is recovered.

(7) 2,3-Dimethyl-7-[1-diethylamino-2-hydroxyethyl) benzofuran 2.77 g (7.68 mmol) of 2,3-dimethyl-7-(1-diethylamino-2-[tert-butyldimethylsilyloxy]ethyl)benzofuran and 30 ml of tetrahydrofuran are introduced into a 250 ml round-bottomed flask. The reaction mixture is cooled to 0° C. by an ice bath and a solution of 2.9 g (9.21 mmol) of tert-butylammonium fluoride trihydrate in 10 ml of tetrahydrofuran is added. The reaction mixture is stirred at 0° C. for 1 hour and at room temperature for 16 hours. 150 ml of water are added and extraction is carried out with ethyl ether (3×200 ml). The organic phases are combined, dried over magnesium sulphate and concentrated under vacuum. The residue is purified by chromatography on a silica column (elution solvent: 5% methanol in dichloromethane). 1.6 g (Yield: 80%) of 2,3-dimethyl-7-(1-diethylamino-2-hydroxyethyl)benzofuran are obtained in the form of an oil.

(8) 2,3-Dimethyl-7-(1-diethylamino-2-hydroxyethyl) benzofuran hydrochloride 0.55 mg of 2,3-dimethyl-7-(1-diethylamino-2-hydroxyethyl)benzofuran and 100 ml of a 0.1N solution of hydrochloric acid in isopropanol are placed in a 100 ml round-bottom flask. The salt is concentrated under vacuum and recrystallized from ethyl acetate. 0.561 g of 2,3-dimethyl-7-(1-diethylamino-2-hydroxyethyl)benzofuran hydrochloride is obtained. M.p.=160–161° C.

EXAMPLE 2

Asymmetric Synthesis

By using essentially the same process as that in Example 1, using in stage (4) AD-mix-α for the (+) isomer, according to the procedure described by Sharpless, K. B. et al., J. Org. Chem., 1992, 57, 2768 (AD-mix-β for the (−) isomer), chiral compounds of formula (I) in accordance with the invention were prepared. These compounds are those having the numbers 5 to 10 in the table below.

EXAMPLE 3

By using essentially the same process as that in Example 1, using an appropriate amine in stage (6), other compounds of formula (I) in accordance with the invention were prepared. These compounds are those having the numbers 10 to 24 in the table below.

EXAMPLE 4

2,3-Dimethyl-7-[1,2-di(diethylamino)ethyl] benzofuran hydrochloride (1) 2,3-Dimethyl-7-[1,2-di(diethylaminoethyl)ethyl] benzofuran 0.8 g (2.7 mmol) of 2,3-dimethyl-7-(1-diethylamino-2-hydroxyethyl)benzofuran, 2.67 ml (19.2 mmol) of triethylamine and 50 ml of dichloromethane are placed in a 100 ml round-bottomed flask. The solution is cooled to −30° C. using a dry ice bath and 99 ml (12.8 mmol) of mesyl chloride are added dropwise. The temperature is allowed to return to 0° C. and the solution is concentrated under vacuum. 20 ml of diethylamine are added to the residue and the solution obtained is heated at reflux for 16 hours. The reaction mixture is cooled to room temperature and concentrated under vacuum, 50 ml of water are added and extraction is carried out with ethyl acetate. The organic phases are combined, dried over magnesium sulphate and concentrated under vacuum. The residue is purified by chromatography on a silica column (elution solvent: 10% methanol in dichloroethane). 0.434 g (Yield: 55%) of 2,3-dimethyl-7-[1,2-di(diethylamino)ethyl]benzofuran is obtained in the form of an oil.

(2) 2,3-Dimethyl-7-[1,2-di(diethylamino)ethyl]benzofuran hydrochloride 400 mg of 2,3-dimethyl-7-[1,2-di(diethylamino)ethyl] benzofuran and 10 ml of a solution of hydrochloric acid in isopropanol are placed in a 100 ml round-bottomed flask. The salt is concentrated under vacuum and recrystallized from ethyl acetate. 400 mg (Yield: 88%) of 2,3-dimethyl-7-[1,2-di(diethylamino)ethyl]benzofuran hydrochloride are obtained. M.p.=183° C.

EXAMPLE 5

By using essentially the same process as that in Example 4, using the appropriate nucleophile, other compounds of formula (I) in accordance with the invention were prepared. These compounds are those having the numbers 27 to 34 in the table below.

EXAMPLE 6

2.3-Dimethyl-7-(1-diethylamino-2-fluoroethyl) benzofuran hydrochloride (1) 2,3-Dimethyl-7-(1-diethylamino-2-fluoroethyl) benzofuran 0.664 ml (3.72 mmol) of diethylaminosulphur trifluoride (DAST) and 5 ml of dichloromethane are placed in a 50 ml round-bottomed flask. The mixture is cooled to −78° C. by a bath of dry ice in acetone and a solution of 0.877 g (3.38 mmol) of 2,3-dimethyl-7-(1-diethylamino-2-hydroxyethyl) benzofuran id 5 ml of dichloroethane is added dropwise. Stirring is continued for 90 minutes at this temperature, before allowing the reaction mixture to return to room temperature. 10 ml of water are added and extraction is carried out with dichloroethane (3×15 ml). The organic phases are combined, dried over magnesium sulphate and concentrated under vacuum. The residue is purified by chromatography on a silica column (elution solvent: 5% methanol in dichloromethane). 700 mg (Yield: 62%) of 2,3-dimethyl-7-(1-diethylamino-2-fluoroethyl)benzofuran hydrochloride are obtained in the form of a colourless oil.

EXAMPLE 7

2-Ethyl-3-methyl-7-(1-diethylamino-2-hydroxyethyl)benzofuran hydrochloride (1) Ethyl 2-(2-ethyl-3-methylbenzofuran-7-yl)-2-(diethylamino) acetate This compound is prepared from 2-ethyl-3-methyl-7-bromobenzofuran according to the procedure of Katrizky, A. R., Urogdi, L. and Mayence, A., Synthesis, 1989, 323.

(2) 2-Ethyl-3-methyl-7-(1-diethylamino-2-hydroxyethyl) benzofuran 300 mg (7.87 mmol) of lithium aluminium hydride and 10 ml of anhydrous tetrahydrofuran are introduced into a 100 ml round-bottomed flask. This suspension is cooled to 0° C. by an ice bath and a solution of 1 g (3.15 mmol) of ethyl 2-(2-ethyl-3-methylbenzofuran-7-yl)-2-(diethylamino) acetate in 20 ml of tetrahydrofuran is added dropwise. The reaction mixture is stirred for 1 hour at room temperature and then hydrolysed by the successive addition of 0.3 ml of water, 0.3 ml of a 15% sodium hydroxide solution and 0.9 ml of water. A white precipitate is formed which is filtered off and washed with 50 ml of ether. The filtrate is washed with 50 ml of water, dried over magnesium sulphate and concentrated under vacuum. The residue is purified by chromatography on a silica column (elution solvent: 2% methanol in dichloromethane). 0.83 g (Yield: 96%) of 2-ethyl-3-methyl-7-(1-diethylamino-2-hydroxyethyl) benzofuran is obtained in the form of a yellow oil.

(3) 2-Ethyl-3-methyl-7-(1-diethylamino-2-hydroxyethyl) benzofuran hydrochloride 0.79 g (2.86 mmol) of 2-ethyl-3-methyl-7-(1-diethylamino-2-hydroxyethyl)benzofuran and 50 ml of a 0.1N solution of hydrochloric acid in isopropanol are placed in 100 ml round-bottomed flask. The salt is concentrated under vacuum. 0.29 g of 2-ethyl-3-methyl-7-(1-diethylamino-2-hydroxyethyl)benzofuran hydrochloride is obtained in the form of a white wax.

EXAMPLE 8

2.3-Dimethyl- 7-[1-(diethylamino)ethyl]benzofuran hydrochloride (1) 2,3-Dimethyl-7-formylbenzofuran 17 g (75.6 mmol) of 2,3-dimethyl-7-bromobenzofuran and 250 ml of tetrahydrofuran are introduced under an inert atmosphere into a 1 liter round-bottomed flask. The mixture is cooled to −78° C. by a bath of dry ice in acetone. 60 ml of tert-butyllithium (1.4M in pentane) are added dropwise and the reaction mixture is allowed to stir for 10 minutes. 17.5 ml of N,N-dimethylformamide (227 mmol) are then added dropwise and the reaction mixture is allowed to return to room temperature. 100 ml of water are added and then extraction is carried out with ethyl acetate (3×80 ml). The organic phases are combined, dried over magnesium sulphate and concentrated. The residue is purified by chromatography on a silica column (elution solvent cyclohexane: ethyl acetate 9:1). 11.97 g (Yield: 91%) of 2,3-dimethyl-7-formylbenzofuran are obtained. M.p. =56–58° C.

(2) 2,3-Dimethyl-7-[1-(diethylamino)ethyl]benzofuran 1.8 g (10.3 mmol) of 2,3-dimethyl-7 -formylbenzofuran, 80 ml of benzene, 4A molecular sieve and 3.19 ml (30.8 mmol) of diethylamine are introduced into a 250 ml three-necked flask equipped with a reflux condenser. The mixture is heated at reflux for 16 hours, cooled to room temperature and then filtered to remove the molecular sieve. The filtrate is concentrated under vacuum and is introduced, with 100 ml of anhydrous tetrahydrofuran, into a 250 ml three-necked flask equipped with a reflux condenser. The solution is cooled to 0° C. by an ice bath and 20 ml of a 3.0 molar solution of methylmagnesium bromide in tetrahydrofuran are added. The reaction mixture is heated at reflux for 26 hours, 8 ml of a 3.0 molar solution of methylmagnesium bromide in tetrahydrofuran are again added and stirring is continued under reflux for 12 hours. The mixture is cooled by an ice bath, 50 ml of a saturated ammonium chloride solution are added and extraction is carried out with ethyl acetate (3×200 ml). The organic phases are combined, dried over magnesium sulphate and concentrated under vacuum. The residue is purified by chromatography on a silica column (elution solvent: 5% methanol in dichloromethane). 0.281 g (Yield: 11%) of 2,3-dimethyl-7-[1-(diethylamino) ethyl]benzofuran is obtained in the form of a colourless oil.

(3) 2,3-Dimethyl-7-[1-(diethylamino)ethyl]benzofuran hydrochloride 0.2 g (0.81 mmol) of 2,3-dimethyl-7-[1-(diethylamino) ethyl]benzofuran and 2 ml of a 6N solution of hydrochloric acid in isopropanol are placed in a 100 ml round-bottomed flask. The salt is concentrated under vacuum and recrystallized from ethyl acetate and diisopropyl ether. 0.142 g (Yield: 61%) of 2,3-dimethyl-7-[1-(diethylamino)ethyl] benzofuran hydrochloride is obtained in the form of a solid. M.p.=28–30° C.

EXAMPLE 9

(+)-2-Ethyl-3-methyl-7-(1-diethylamino-2-hydroxyethyl)benzothiophene hydrochloride (1) (2-Bromothiophenoxy)acetone 20 g (105.7 mmol) of 2-bromothiophenol, 19 g (137.5 mmol) of potassium carbonate, 27.8 g (165.5 mmol) of potassium iodide, 200 ml of dimethylformamide and 14.68 g (158.6 mmol) of chloroacetone are introduced into a 500 ml three-necked flask. The mixture is stirred for 2 hours at room temperature and is then poured into 800 ml of water. Extraction is carried out with ethyl acetate (3×400 ml). The organic phases are combined, washed with a molar sodium hydroxide solution (2×400 ml), dried over magnesium sulphate and concentrated. The residue is purified by chromatography on a silica column (elution solution: 10% ethyl acetate in cyclohexane). 24.1 g (Yield: 93%) of (2-bromothiophenoxy)acetone are obtained (yellow oil).

(2) 3-Methyl-7-bromobenzothiophene 140 g of polyphosphoric acid (PPA) and 14.4 g (58.7 mmol) of (2-bromothiophenoxy)acetone are placed in a 500 ml three-necked flask. The mixture is heated at 100° C. for 40 minutes and then cooled in an ice bath. Crushed ice is added and extraction is carried out with ethyl acetate (3×300 ml). The organic phases are combined, washed with water (200 ml) and then with a molar sodium hydroxide solution (200 ml), dried over magnesium sulphate and then concentrated. The residue is purified by chromatography on a silica column (elution solution: cyclohexane). 11.86 g (Yield: 89%) of 3-methyl-7-bromobenzothiophene are obtained in the form of an oil.

(3) 2-Acetyl-3-methyl-7-bromobenzothiophene 7.6 g (39.46 mmol) of 3-methyl-7-bromobenzothiophene (dried beforehand under vacuum over phosphorus pentoxide) and 70 ml of dichloromethane are placed in a 250 ml three-necked flask equipped with a thermometer. The mixture is cooled to 0° C. by an ice bath, 2.89 g (36.8 mmol) of acetyl chloride are added and then the reaction mixture is stirred for 5 minutes at 0 °C. 5 g of aluminium chloride are then added in small portions, the temperature being controlled so that it does not exceed 70° C., and stirring is continued at 0° C. for 45 minutes. The reaction mixture is poured onto crushed ice and extraction is carried out with ethyl acetate (3×150 ml). The organic phases are combined, washed with a saturated sodium bicarbonate solution (200 ml) and water (200 ml), dried over magnesium sulphate and then concentrated. The residue is purified by chromatography on a silica column (elution solvent: 5% ethyl acetate in petroleum ether). 8.55 g (Yield: 95%) of 2-acetyl-3-methyl-7-bromobenzothiophene are obtained in the form of a white solid. M.p.=105–107° C.

(4) 2-Ethyl-3-methyl-7-bromobenzothiophene 8.6 g (32 mmol) of 2-acetyl-3-methyl-7-bromobenzothiophene and 175 ml of diethylene glycol are placed in a 500 ml three-necked flask equipped with a distillation system. The mixture is stirred at 30° C. for 5 minutes and 4.2 ml (56 mmol) of hydrazine monohydrate are added dropwise. The mixture is heated at 40° C. for 5 minutes and 4.3 g (76.6 mmol) of powdered potassium hydroxide are added. The temperature is brought to 110° C. for 40 minutes and then to a 160° C. for 100 minutes, in order to allow the water present in the reaction mixture to be distilled off. The mixture, once cooled, is then poured onto crushed ice and extraction is carried out with ethyl acetate (3×200 ml). The organic phases are combined, washed with 200 ml of a saturated sodium bicarbonate solution and 2×200 ml of water, dried over magnesium sulphate and concentrated. The residue is purified by chromatography on a silica column (elution solvent: cyclohexane). 7.62 g (Yield: 84%) of 2-ethyl-3-methyl-7-bromobenzothiophene are obtained in the form of a yellow oil.

By using essentially the same process as that in Stages (4) to (8) of Example 1 and by using, in Stage (4), AD-mix-a for the (+) isomer, according to the procedure described by Sharpless, K. B. et al., J. Org. Chem., 1992, 57, 2768, the chiral benzothiophene compounds of formula (I) in accordance with the invention were prepared.

TABLE

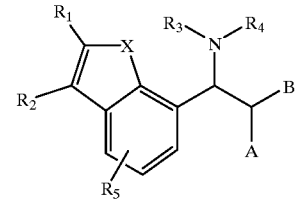

(I)

| No. | X | $R_1$ | $R_2$ | $R_3$ | $R_4$ | $R_5$ | A | B | Salt | M.p. (° C.) |
|---|---|---|---|---|---|---|---|---|---|---|
| 1 | O | $CH_3$ | $CH_3$ | $C_2H_5$ | $C_2H_5$ | H | OH | H | - - | oil |
| 2 | O | $CH_3$ | $CH_3$ | $C_2H_5$ | $C_2H_5$ | H | OH | H | HCl | 160 |
| 3 | O | —$(CH_2)_4$— | | $C_2H_5$ | $C_2H_5$ | H | OH | H | - - | oil |
| 4 | O | —$(CH_2)_4$— | | $C_2H_5$ | $C_2H_5$ | H | OH | H | HCl | 126 |
| 5+ | O | $CH_3$ | $CH_3$ | $C_2H_5$ | $C_2H_5$ | H | OH | H | - - | oil |
| 6+ | O | $CH_3$ | $CH_3$ | $C_2H_5$ | $C_2H_5$ | H | OH | H | HCl | 176 |
| 7− | O | $CH_3$ | $CH_3$ | $C_2H_5$ | $C_2H_5$ | H | OH | H | - - | oil |
| 8− | O | $CH_3$ | $CH_3$ | $C_2H_5$ | $C_2H_5$ | H | OH | H | HCl | 180 |
| 9− | O | $C_2H_5$ | $CH_3$ | $C_2H_5$ | $C_2H_5$ | H | OH | H | - - | oil |
| 10+ | O | $C_2H_5$ | $CH_3$ | $C_2H_5$ | $C_2H_5$ | H | OH | H | HCl | 128 |
| 11 | O | $CH_3$ | $CH_3$ | $C_2H_5$ | $C_3H_7$ | H | OH | H | - - | oil |
| 12 | O | $CH_3$ | $CH_3$ | $C_2H_5$ | $C_3H_7$ | H | OH | H | HCl | 162 |
| 13 | O | $CH_3$ | $CH_3$ | —$(CH_2)_5$— | | H | OH | H | - - | oil |
| 14 | O | $CH_3$ | $CH_3$ | —$(CH_2)_5$— | | H | OH | H | HCl | 223 |
| 15 | O | $CH_3$ | $CH_3$ | —$(CH_2)_2$—O—$(CH_2)_2$— | | H | OH | H | - - | oil |
| 16 | O | $CH_3$ | $CH_3$ | —$(CH_2)_2$—O—$(CH_2)_2$— | | H | OH | H | HCl | 238 |
| 17 | O | $CH_3$ | $CH_3$ | —$(CH_2)_2$—N($CH_3$)—$(CH_2)_2$— | | H | OH | H | - - | oil |
| 18 | O | $CH_3$ | $CH_3$ | —$(CH_2)_2$—N($CH_3$)—$(CH_2)_2$— | | H | OH | H | HCl | 242 |
| 19 | O | $CH_3$ | $CH_3$ | $CH_3$ | $CH_3$ | H | OH | H | - - | 0 |
| 20 | O | $CH_3$ | $CH_3$ | $CH_3$ | $CH_3$ | H | OH | H | HCl | 159 |
| 21 | O | $CH_3$ | $CH_3$ | $CH_3$ | $C_2H_5$ | H | OH | H | - - | oil |
| 22 | O | $CH_3$ | $CH_3$ | $CH_3$ | $C_2H_5$ | H | OH | H | HCl | 148 |
| 23 | O | $CH_3$ | $CH_3$ | —$(CH_2)_4$— | | H | OH | H | - - | oil |
| 24 | O | $CH_3$ | $CH_3$ | —$(CH_2)_4$— | | H | OH | H | HCl | 192 |
| 25 | O | $CH_3$ | $CH_3$ | $C_2H_5$ | $C_2H_5$ | H | $N(C_2H_5)_2$ | H | - - | oil |
| 26 | O | $CH_3$ | $CH_3$ | $C_2H_5$ | $C_2H_5$ | H | $N(C_2H_5)_2$ | H | HCl | 183 |
| 27 | O | $CH_3$ | $CH_3$ | $C_2H_5$ | $C_2H_5$ | H | $NHCH_3$ | H | - - | oil |
| 28 | O | $CH_3$ | $CH_3$ | $C_2H_5$ | $C_2H_5$ | H | $NHCH_3$ | H | HCl | 192 |
| 29 | O | $CH_3$ | $CH_3$ | $C_2H_5$ | $C_2H_5$ | H | $N_3$ | H | - - | oil |
| 30 | O | $CH_3$ | $CH_3$ | $C_2H_5$ | $C_2H_5$ | H | $N_3$ | H | HCl | 174 |
| 31 | O | $CH_3$ | $CH_3$ | $C_2H_5$ | $C_2H_5$ | H | $NH_2$ | H | - - | oil |
| 32 | O | $CH_3$ | $CH_3$ | $C_2H_5$ | $C_2H_5$ | H | $NH_2$ | H | HCl | 238 |
| 33 | O | $CH_3$ | $CH_3$ | $C_2H_5$ | $C_2H_5$ | H | SH | H | - - | oil |
| 34 | O | $CH_3$ | $CH_3$ | $C_2H_5$ | $C_2H_5$ | H | SH | H | HCl | 114 |
| 35 | O | $CH_3$ | $CH_3$ | $C_2H_5$ | $C_2H_5$ | H | F | H | - - | oil |
| 36 | O | $CH_3$ | $CH_3$ | $C_2H_5$ | $C_2H_5$ | H | F | H | HCl | 112 |
| 37 | O | $C_2H_5$ | $CH_3$ | $C_2H_5$ | $C_2H_5$ | H | $OC_2H_5$ | =O | - - | oil |
| 38 | O | $C_2H_5$ | $CH_3$ | $C_2H_5$ | $C_2H_5$ | H | $OC_2H_5$ | =O | $(HOOC)_2$ | 139 |
| 39 | O | $C_2H_5$ | $CH_3$ | $C_2H_5$ | $C_2H_5$ | H | OH | H | - - | oil |
| 40 | O | $C_2H_5$ | $CH_3$ | $C_2H_5$ | $C_2H_5$ | H | OH | H | HCl | wax |
| 41 | O | $CH_3$ | $CH_3$ | $C_2H_5$ | $C_2H_5$ | H | H | H | - - | oil |
| 42 | O | $CH_3$ | $CH_3$ | $C_2H_5$ | $C_2H_5$ | H | H | H | HCl | 28 |
| 43 | O | $CH_3$ | $CH_3$ | $C_2H_5$ | $C_2H_5$ | H | H | $OCH_3$ | - - | oil |

TABLE-continued

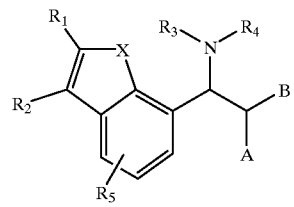

(I)

| No. | X | R₁ | R₂ | R₃ | R₄ | R₅ | A | B | Salt | M.p. (°C.) |
|---|---|---|---|---|---|---|---|---|---|---|
| 44 | O | CH₃ | CH₃ | C₂H₅ | C₂H₅ | H | H | OCH₃ | HCl | 100 |
| 45 | O | CN | CH₃ | C₂H₅ | C₂H₅ | H | OH | H | -- | oil |
| 46 | O | CN | CH₃ | C₂H₅ | C₂H₅ | H | OH | H | HCl | 177 |
| 47 | O | CONH₂ | CH₃ | C₂H₅ | C₂H₅ | H | OH | H | -- | oil |
| 48 | O | CONH₂ | CH₃ | C₂H₅ | C₂H₅ | H | OH | H | HCl | 197 |
| 49⁻ | O | C₂H₅ | CH₃ | C₂H₅ | C₂H₅ | F | OH | H | -- | oil |
| 50⁺ | O | C₂H₅ | CH₃ | C₂H₅ | C₂H₅ | F | OH | H | HCl | 130 |
| 51⁺ | O | C₂H₅ | CH₃ | C₂H₅ | C₂H₅ | H | OH | H | -- | oil |
| 52⁻ | O | C₂H₅ | CH₃ | C₂H₅ | C₂H₅ | H | OH | H | HCl | 134 |
| 53 | O | CH₃ | CH₃ | C₂H₅ | C₂H₅ | H | N(OCH₃)CH₃ | =O | -- | oil |
| 54 | O | CH₃ | CH₃ | C₂H₅ | C₂H₅ | H | N(OCH₃)CH₃ | =O | HCl | 53 |
| 55 | O | CH₃ | CH₃ | C₂H₅ | C₂H₅ | H | OH | Ph | -- | oil |
| 56 | O | CH₃ | CH₃ | C₂H₅ | C₂H₅ | H | OH | Ph | HCl | 219 |
| 57 | O | CH₃ | CH₃ | C₂H₅ | C₂H₅ | H | OH | C₂H₅ | -- | oil |
| 58 | O | CH₃ | CH₃ | C₂H₅ | C₂H₅ | H | OH | C₂H₅ | HCl | 181 |
| 59 | O | CH₃ | CH₃ | C₂H₅ | C₂H₅ | H | OH | i-C₃H₇ | -- | oil |
| 60 | O | CH₃ | CH₃ | C₂H₅ | C₂H₅ | H | OH | i-C₃H₇ | HCl | 194 |
| 61⁺ | O | C₂F₅ | CH₃ | C₂H₅ | C₂H₅ | H | OH | H | -- | oil |
| 62⁺ | O | C₂F₅ | CH₃ | C₂H₅ | C₂H₅ | H | OH | H | HCl | 156 |
| 63⁺ | S | C₂H₅ | CH₃ | C₂H₅ | C₂H₅ | H | OH | H | -- | oil |
| 64⁺ | S | C₂H₅ | CH₃ | C₂H₅ | C₂H₅ | H | OH | H | HCl | 173 |

In this table:

"--" represents a compound in the free form.

Moreover, the compounds where the number is accompanied by a "+" are in the (+) form and those accompanied by a "-" are in the (-) form. The $[\alpha]_D^{20}$ (C=1) values of the compounds 5, 6, 7, 8, 9, 10, 49, 50 51, 52, 61, 62, 63 and 64 are respectively +24.7 ($CH_2Cl_2$), +3.0 (MeOH), -24.7 ($CH_2Cl_2$), -3.5 (MeOH), -23.9 ($CH_2Cl_2$), +29.0 ($CH_2Cl_2$), -16.6 ($CH_2Cl_2$), +78.9 ($CH_2Cl_2$), +19.5 ($CH_2Cl_2$), -29.5 ($CH_2Cl_2$), -15.9 ($CH_2Cl_2$), +22.7 ($CH_2Cl_2$), +15.22 ($CH_2Cl_2$) and +16.3 ($CH_2Cl_2$). All the compounds in the table are racemates.

The compounds of the invention were subjected to biological tests intended to demonstrate their contractile activity on urethral and arterial smooth muscles.

1. The in vitro activity of the compounds of the invention was studied on urethral and arterial smooth muscles. These tests were carried out on female New Zealand rabbits weighing from 3 to 3.5 kg. The animals were killed by vertebral dislocation and then rings of tissue from the mesenteric arteries and from the urethra were removed. These rings of tissue were immersed in a modified Krebs solution oxygenated by a mixture of 95% $O_2$ and 5% $CO_2$. Each tissue sample was subjected to a tension of 1 g, phenylephrine was then introduced in cumulative doses and the dose/response curve was drawn up. After rinsing the samples, the compound to be studied was introduced in cumulative doses and the dose/response curve was drawn up. The contractile effect of each compound is evaluated by the calculation of the $PD_2$ (negative logarithm of the agonist concentration which induces 50% of the maximum contraction) and by the maximum effect representing the percentage of the maximum contraction obtained with phenylephrine (% $E_{max}$).

The results obtained show that the compounds in accordance with the invention exhibit:

a urethral $pD_2$ usually of between 4 and 9 an arterial $pD_2$ usually of less than 3, a urethral % $E_{max}$ of more than 30, usually between 40 and 90, an arterial % $E_{max}$ usually of less than 5.

2. The in vitro activity of the compounds of the invention were studied on the saphenous veins of the Yucatan miniature pig. The tissue is cut into a helix and is mounted in an isolated organ tank in a modified Krebs solution oxygenated by a mixture of 95% $O_2$ and 5% $CO_2$ held at 37° C. The vessel is connected to an isometric sensor under a basal tension of 1 g and is connected to a polygraph which makes it possible to record variations in tension. The viability of each preparation is tested by prestimulation with 3 μM noradrenaline. After rinsing, the compound to be studied is introduced and its concentration/response curve constructed cumulatively until a maximum response is obtained. The contractile effect of each compound is evaluated by calculation of the $EC_{50}$ (concentration producing 50% of the maximum response).

The compounds of the invention have made it possible to obtain a venoconstrictive activity with an $EC_{50}$ value usually of between 1 μM and 100 μM.

The compounds of the invention can be used in the treatment of venous insufficiency and of venous ulcers.

3. The in vivo activity of the compounds of the invention on blood and urethral pressure was studied in the amyelous rat and the rabbit, according to the following protocols:

Pithed Rats

Wistar rats are anaesthetized and pithed (according to the technique described by Gillespie, MacLaren A. and Polock D., A method of stimulating different segments of the autonomic outflow from the spinal column to various organs in the pithed cat and rat; Br. J. Pharmacol., 1970, 40: 257–267).

Catheters are introduced via the femoral artery and a jugular vein. Another catheter is introduced into the urethra via an incision made in the bladder. The compounds to be tested are administered at increasing doses via intravenous infusion.

The results are expressed in doses (μg/kg) necessary to increase the urethral pressure by 10 cm of water ($UP_{10}$) or the arterial pressure by 10 mm of Hg ($AP_{10}$) or by 50 mm of Hg ($AP_{50}$).

The compounds of the invention, thus tested, made it possible to obtain:

an $UP_{10}$ with doses of less than 500 μg/kg, usually of between 5 and 200 μg/kg, an $AP_{10}$ with doses of greater than 600 μg/kg, usually of between 600 and 2000 μg/kg, the $AP_{50}$ could not be reached.

Rabbits Which Are Awake

The experiments are carried out on female New Zealand rabbits weighing between 3 and 4 kg anaesthetized by a mixture of ketamine and xylazine. The catheters are introduced via the descending part of the aorta into the femoral artery, into a jugular vein and into the urethra (1.5 cm below the neck of the bladder).

The compounds to be tested are administered 5 to 15 days following the operation by intravenous (i.v.) administration over 5 minutes and in a single dose (of 10 or 100 μg/kg). The compounds to be tested by the oral route are administered by the force-feeding of a single dose (of 10, 30, 100, 300 or 1000 μg/kg).

In this instance, the increase in the urethral pressure (UP) and in the arterial pressure (AP) were measured with respect to the urethral basal pressure and the arterial basal pressure respectively. The results obtained are expressed as percentage of premedication values at 5 minutes after intravenous (i.v.) administration and 30 minutes after force-feeding (p.o.).

The compounds of the invention, thus tested, made possible an increase in the UP of more than 50%, usually of between 50 and 350% after intravenous administration and usually of between 50 and 200% after force-feeding. The increase in the AP was always less than 10% and is usually 0%.

The combined results above show that the compounds of the invention have a strong urethral contractile action and a weak arterial contractile action.

They can be used as a medicament, in particular as an agent for contracting smooth muscles, and more particularly still in the treatment of urinary stress incontinence. In this indication, the compounds according to the invention are highly effective and usually exhibit fewer side effects than the medicaments conventionally used for such a treatment, in particular as regards side effects affecting the cardiovascular system, in particular the arterial beds.

The compounds according to the invention can also be employed in the treatment of venous insufficiencies, migraine or gastrointestinal disorders and as a vasoconstrictor for the mucous membrane of the nose.

The compounds according to the invention can be presented in various pharmaceutical forms appropriate for administration via the digestive or parenteral route, if appropriate in combination with at least one pharmaceutical excipient. The appropriate pharmaceutical forms are, for example, tablets, capsules, including hard gelatin capsules, sugar-coated tablets, solutions to be taken orally, injectable solutions, syrups or suppositories.

These pharmaceutical forms can contain a dose which makes possible a daily dose of 0.1 μg/kg to 50 mg/kg.

What is claimed is:

1. A compound of formula (I)

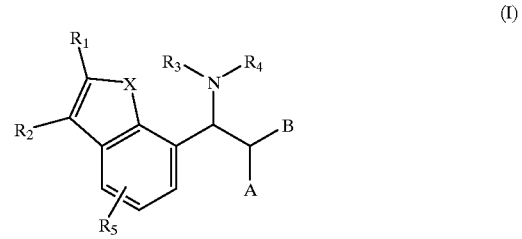

in which:

A represents either a hydrogen atom, a hydroxyl, a $C_{1-6}$ hydroxyalkyl group, a thiol, a $C_{1-6}$ alkylsulphanyl group, an amino group, a $C_{1-6}$ alkylamino group, a di($C_{1-6}$ alkyl)amino group, a $C_{1-6}$ alkylhydroxylamine group, a $C_{1-6}$ alkoxy group, a hydroxylamine group, an N,O-di($C_{1-6}$ alkyl)hydroxylamine group, an azido or a halogen, B represents a hydrogen atom, a linear or branched $C_{1-6}$ alkyl group, a $C_{2-6}$ alkenyl group, a $C_{1-6}$ fluoroalkyl group, a $C_{1-2}$ perfluoroalkyl group, a $C_{1-6}$ alkoxy group, a phenyl group or an oxo group, X represents an oxygen or sulphur atom, $R_1$ and $R_2$ represent, independently of one another, a hydrogen atom, a halogen, a cyano, a carboxamide, a linear or branched $C_{1-6}$ alkyl group, a $C_{2-6}$ alkenyl group, a $C_{3-6}$ cycloalkyl group, a $C_{1-6}$ alkoxycarbonyl group, a $C_{1-6}$ hydroxyalkyl group, a $C_{1-6}$ alkoxy group, a $C_{1-6}$ alkoxyalkyl group, a $C_{1-6}$ fluoroalkyl group or a $C_{1-2}$ perfluoroalkyl group, $R_3$ and $R_4$ represent, independently of one another, a hydrogen atom, a $C_{1-6}$ alkyl group, a $C_{2-6}$ alkenyl group, a $C_{3-6}$ cycloalkyl group, a $C_{3-6}$cycloalkenyl group, a $C_{1-6}$ fluoroalkyl group or a $C_{1-2}$ perfluoroalkyl group, and $R_5$ represents a hydrogen atom or a halogen, or pharmaceutically acceptable acid addition salts of the compounds of formula (I), wherein the compounds of formula (I) can be in the form of an enantiomer, a diasteroisomer or of a mixture of these different forms.

2. A compound of claim 1, wherein $R_5$ represents fluorine, chlorine, bromine.

3. A pharmaceutical composition, comprising a compound of claim 1 together with a pharmaceutically acceptable carrier.

4. A composition for treating urinary stress incontinence, comprising an effective amount of a compound of claim 1 together with a pharmaceutically acceptable carrier.

5. A method of treating urinary stress incontinence, comprising administering to host in need thereof an effective amount of a compound of claim 1.

6. A composition for treating venous insufficiencies, comprising an effective amount of a compound of claim 1 together with a pharmaceutically acceptable carrier.

7. A method of treating venous insufficiencies, comprising administering to host in need thereof an effective amount of a compound of claim 1.

8. A composition for treating venous ulcers, comprising an effective amount of a compound of claim 1 together with a pharmaceutically acceptable carrier.

9. A method of treating venous ulcers, comprising administering to host in need thereof an effective amount of a compound of claim 1.

10. A composition for treating gastrointestinal disorders, comprising an effective amount of a compound of claim 1 together with a pharmaceutically acceptable carrier.

11. A method of treating gastrointestinal disorders, comprising administering to host in need thereof an effective amount of a compound of claim 1.

12. A composition for treating migraines, comprising an effective amount of a compound of claim 1 together with a pharmaceutically acceptable carrier.

13. A method of treating migraines, comprising administering to host in need thereof an effective amount of a compound of claim 1.

14. A composition for treating the mucous membrane of the nose, comprising a vascoconstrictive effective amount of a compound of claim 1 together with a pharmaceutically acceptable carrier.

15. A method of treating mucous membrane of the nose, comprising administering to host in need thereof a vasoconstrictive effective amount of a compound of claim 1.

16. A process for preparing a compound of claim 1 in which A is a hydroxyl group, comprising:

(A) reacting a compound of formula II,

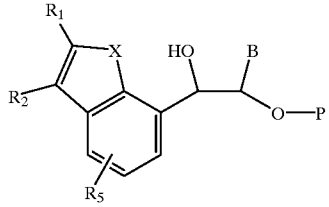

wherein $R_1$, $R_2$ and $R_5$ are as defined in claim 1 and P is a protecting group, with an amine of formula $HNR_3R_4$, wherein $R_3$ and $R_4$ are as defined in claim 1; and (B) deprotecting the product of the reaction in step A.

17. A process for preparing a compound of claim 1 in which A is a hydroxyl group, comprising reacting a compound of formula (XV)

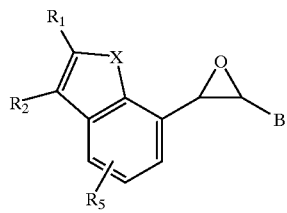

in which $R_1$, $R_2$, $R_5$ and B are as defined in claim 1, with an amine of formula $HNR_3R_4$, in which $R_3$ and $R_4$ are as defined in claim 1.

18. A process for preparing a compound of claim 1 in which A is a hydroxyl group, comprising reacting a compound of formula XVIII

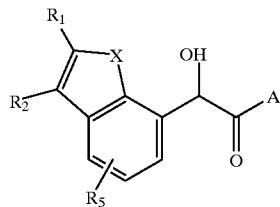

in which $R_1$, $R_2$ and $R_5$ are as defined in claim 1 and A represents a $C_{1-6}$ alkoxy group, with an amine of formula $HNR_3R_4$, in which $R_3$ and $R_4$ are as defined in claim 1.

19. A process for preparing a compound of claim 1 in which A is not a hydroxyl group, comprising reacting a compound of formula XIX

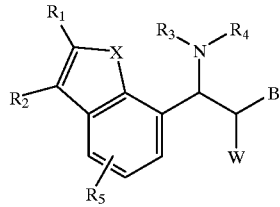

in which $R_1$, $R_2$, $R_3$, $R_4$ and $R_5$ are as defined in claim 1 and W is a nucleofuge group, with a nucleophilic group A as defined in claim 1.

20. A process for preparing a compound of claim 1 in which A is a hydrogen atom, comprising reacting a compound of formula XX

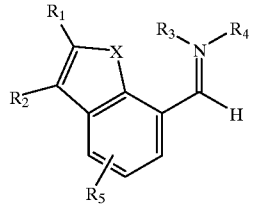

in which $R_1$, $R_2$, $R_3$, $R_4$ and $R_5$ are as defined in claim 1, with a nucleophilic group $B\text{-}CH_2MY$, wherein B is as defined in claim 1, Y represents a halogen, and M represents a metal.

21. A compound of formula (I) as claimed in claim 1, wherein A is fluorine, chlorine or bromine.

22. A compound of formula (I) as claimed in claim 1, wherein $R_1$, $R_2$, or both $R_1$ and $R_2$ are fluorine, chlorine, or bromine.

23. A racemic mixture of compounds as claimed in claim 1.

* * * * *